US00PP14567P29

(12) United States Plant Patent
Kaagman

(10) Patent No.: US PP14,567 P2
(45) Date of Patent: Feb. 24, 2004

(54) DAHLIA PLANT NAMED 'DADA PINK'

(50) Latin Name: *Dahlia variabilis*
Varietal Denomination: Dada Pink

(75) Inventor: Pim Kaagman, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/404,823

(22) Filed: Apr. 1, 2003

(51) Int. Cl.[7] ..... A01H 5/00
(52) U.S. Cl. ..... Plt./321
(58) Field of Search ..... Plt./321

*Primary Examiner*—Bruce R. Campell
*Assistant Examiner*—A Para
(74) *Attorney, Agent, or Firm*—Jondle & Associates PC

(57) ABSTRACT

A dahlia cultivar particularly distinguished by pink colored flowers, compact habit and good basal branching.

1 Drawing Sheet

Genus and species: *Dahlia variabilis.*
Variety denomination: 'Dada Pink'.

BACKGROUND OF THE NEW PLANT

The present invention comprises a new and distinct cultivar of dahlia, botanically known as *Dahlia variabilis*, and hereinafter referred to by the cultivar name 'Dada Pink'. The new cultivar is asexually reproduced from vegetative cuttings and tissue culture resulting from the cross of the seed/pod parent Dahlstar Rose, an unpatented commercial line×DA-52, a pink proprietary line that is unnamed and unpatented.

'Dada Pink' is a product of a planned breeding program intended to create new dahlia plants with yellow colored flowers, compact habit, good basal branching and moderately vigorous growth.

The new cultivar was created in 1997 in Andijk, The Netherlands and has been asexually reproduced repeatedly by vegetative cuttings and tissue culture in Gilroy, Calif., Andijk, The Netherlands, and Guatemala over a four-year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature inflorescence.

DESCRIPTION OF THE NEW CULTIVAR

The following detailed descriptions set forth the distinctive characteristics of 'Dada Yellow'. The data, which defines these characteristics, were collected from asexual reproductions carried out in Gilroy, Calif. The plant history was taken on 10 months old plants grown in one-gallon pots in fall/winter season, in a poly-covered greenhouse under 2–4 hours supplemental light and color readings were taken in the greenhouse in the winter season under natural light.

Plants had been cut back numerous times prior to data readings taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

Classification:
- *Botanical.*—*Dahlia variabilis.*
- *Commercial.*—Dahlia.

Growth:
- *Form.*—Upright, compact and mounding.
- *Growth and branching habit.*—Good vigorous habit, well branched, full plant.
- *Height.*—From soil level to top of blooms: Approximately 25–30 cm.
- *Width.*—Approximately 35–40 cm including flowers.
- *Time to produce a finished flowering plant.*—9–12 weeks.
- *Outdoor plant performance.*—Fast cropping, free flowering, used in patio planters and mixed container plantings or garden beds.
- *Time to initiate roots.*—Approximately 14–28 days in the greenhouse.
- *Root description.*—Fibrous, white.

Leaves:
- *Arrangement.*—Young foliage leaves are single and mature leaves simple, opposite.
- *Length.*—4.2–5.5 cm.
- *Width.*—3.3–3.7 cm.
- *Leaf blade shape.*—Ovate to Elliptic.
- *Leaf margin.*—Dentate/Ciliate.
- *Apex aspect.*—Acuminate.
- *Base aspect.*—Attenuate.
- *Leaf color.*—Upper surface, RHS 139A (green)but a little darker and Undersurface, RHS 191A (greyed-green) base color, with RHS 138A (green) veining.
- *Texture.*—Occasional hispid with strigulose on veins.
- *Venation.*—Palmate.
- *Venation color.*—RHS 144B (yellow-green).
- *Petiole length.*—3.1–3.8 cm.
- *Petiole width.*—0.2 cm.
- *Petiole color.*—Between RHS 144A and B (yellow-green).
- *Petiole texture.*—Occasionally hispid.

Stem:

*Length.*—25–30 cm.

*Diameter.*—0.4–0.5 cm.

*Internodes length.*—1.2–1.3 cm.

*Color.*—RHS 144A (yellow-green).

*Texture.*—Occasional hispid.

*Stem anthocyanin.*—Yes.

*Peduncle color.*—Between RHS 144A and B (yellow-green).

*Peduncle length.*—3.5–4.5 cm.

*Peduncle diameter.*—0.2 cm.

*Peduncle texture.*—Smooth.

*Peduncle anthocyanin.*—Yes, strong.

Bud:

*Shape.*—Orbicular.

*Diameter.*—1.0–1.2 cm.

*Length.*—1.0 cm.

*Color at tight bud.*—RHS# 145A (yellow-green).

Flower:

*Blooming habit.*—Continuous all through the growing season. Good floriferousness.

*Inflorescence type.*—Borne on terminals above foliage, semi-double flowers, floret faces upward or outward.

*Flower diameter.*—5.7–6.7 cm.

*Ray petal color.*—Front side, RHS N155B (white) base color with RHS 62B (red-purple) overlay occasionally heavier, to RHS N66D (red-purple); RHS 63C (red-purple) vertical striations the length of the petal, occasionally the striations are more heavily a RHS N57D (red-purple) and irregularly RHS 61B (red-purple) striated blotches, and RHS 3B (yellow) at base of petals; Underside, RHS N155B (white) base color with RHS 62C (red-purple) overlay and RHS 63C (red-purple) vertical striations the length of the petal and a shade darker basally. Petal length — 2.5–3.0 cm. Petal width — 1.2–1.6 cm. Petal apex shape — Acute. Petal base shape — Attenuate. Petal margin — Entire, petals recurve inward moderately. Petal texture — Papillose. Petal quantity — 45–60.

*Disc petal color.*—RHS 21A (yellow-orange). Petal length — 0.8–1.0 cm. Petal diameter — 0.2 cm. Petal shape — Elongated, cylindrical, shiny. Petal quantity — 45–50.

*Involucral bracts.*—Usually 5.

*Color*—RHS 189A (greyed-green) base color with thin vertical striations of RHS 139A (green).

*Length.*—1.1–1.2 cm.

*Width.*—0.3–0.4 cm.

*Shape.*—Oblanceolate.

*Apex.*—Acute.

*Texture.*—Hispid basally.

*Lastingness of individual blooms.*—7–12 days.

*Fragrance.*—No.

Reproductive organs:

*Androecium, pollen color.*—RHS 25A (orange).

*Gynoecium, stigma color.*—RHS 4B (yellow).

*Style color.*—RHS 4D (yellow).

*Pistil length.*—1.1–1.3 cm.

*Fruit seed set.*—Not observed.

Disease and insect resistance: Not observed.

COMPARISON WITH KNOWN CULTIVARS

'Dada Pink' differs from the female parent 'Dahlstar Rose' in the following ways: 'Dada Pink' has a pink colored flower, is more double and is earlier to flower than 'Dahlstar Rose'.

'Dada Pink' differs from the male parent DA-52 in the following ways: 'Dada Pink' has smaller flowers, is a dwarf and is more vigorous than DA-52.

I claim:

1. A new and distinct dahlia plant as shown and described herein.

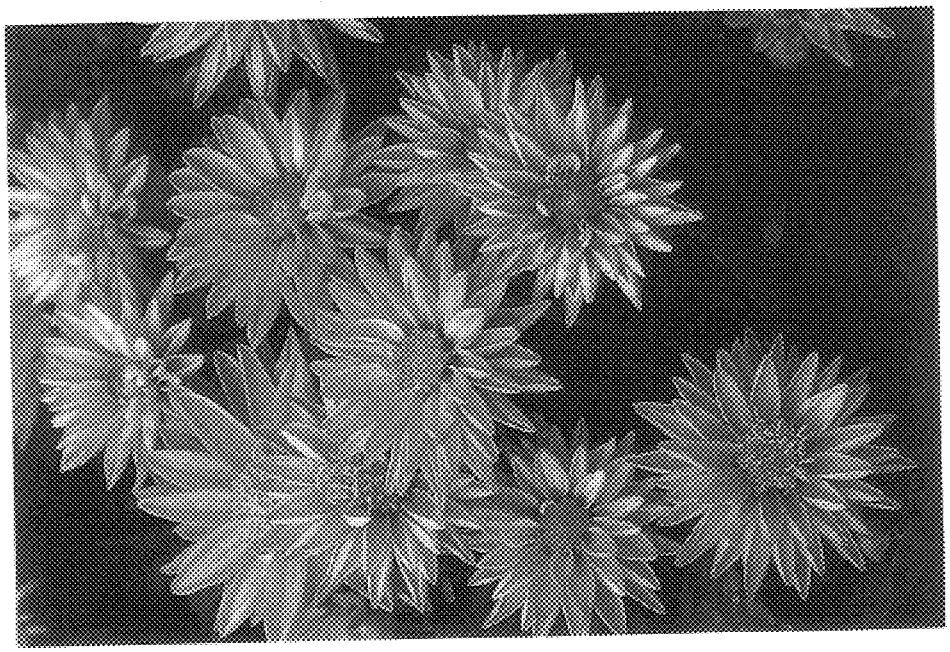

* * * * *